Figure 1:
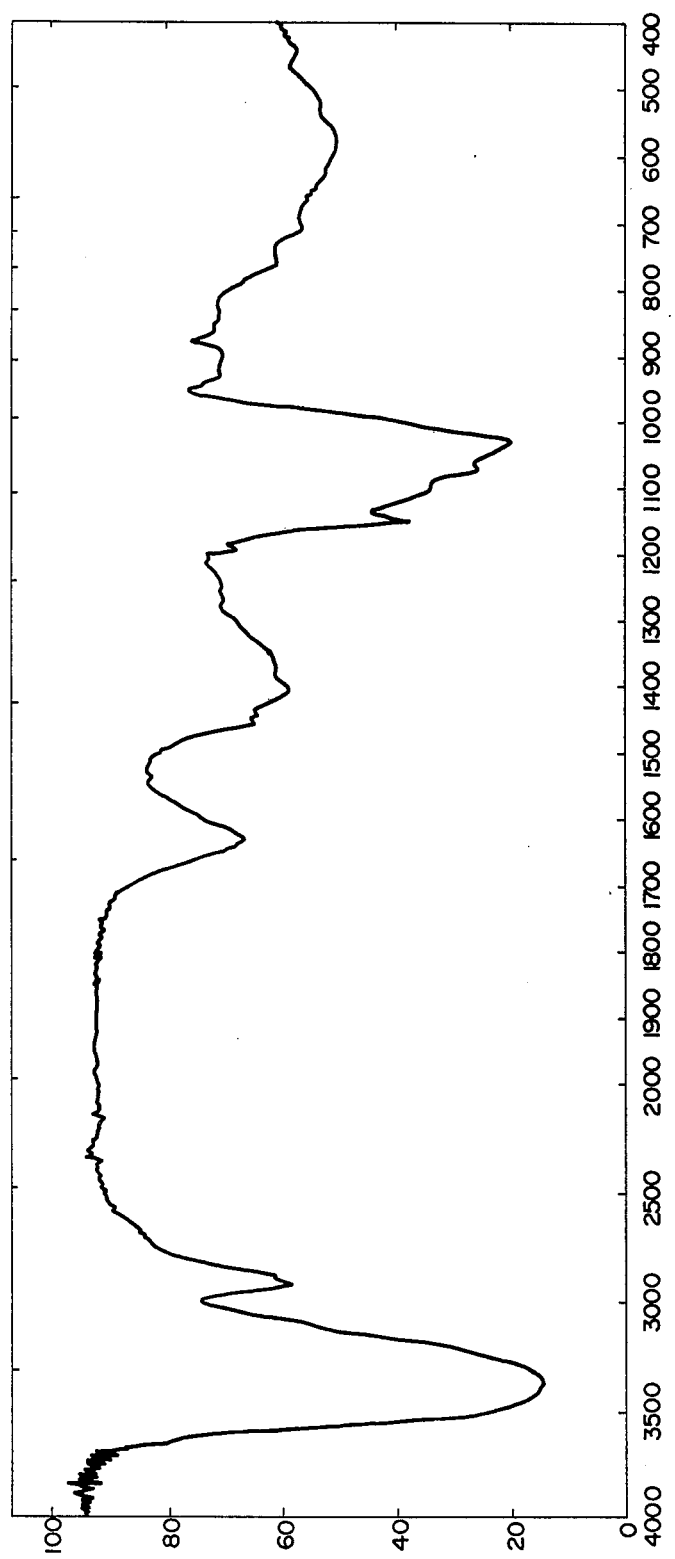

United States Patent [19]

Otani et al.

[11] 4,254,256
[45] Mar. 3, 1981

[54] AMINO SUGAR COMPOUND

[75] Inventors: Masaru Otani; Tetsu Saito; Shuzo Satoi; Junzo Mizoguchi; Naoki Muto, all of Shizuoka, Japan

[73] Assignee: Toyo Jozo company, Ltd., Shizuoka, Japan

[21] Appl. No.: 968,697

[22] Filed: Dec. 12, 1978

[30] Foreign Application Priority Data

Dec. 28, 1977 [JP] Japan ................... 52/157328

[51] Int. Cl.³ ............... A61K 31/73; C07H 5/06
[52] U.S. Cl. ................... 536/18; 435/101; 435/84; 536/1; 536/4; 424/180
[58] Field of Search ............. 531/1; 536/18, 4

[56] References Cited

U.S. PATENT DOCUMENTS

| | | | |
|---|---|---|---|
| 4,010,258 | 3/1977 | Murao | 424/115 |
| 4,062,950 | 12/1977 | Frommer et al. | 424/181 |
| 4,174,439 | 11/1979 | Rauenbusch et al. | 536/18 |
| 4,175,123 | 11/1979 | Junge et al. | 536/4 |

FOREIGN PATENT DOCUMENTS

| | | |
|---|---|---|
| 2614393 | 6/1977 | Fed. Rep. of Germany ............. 536/18 |
| 51-54990 | 5/1976 | Japan ............. 536/18 |
| 52-24119 | 6/1977 | Japan ............. 536/18 |

OTHER PUBLICATIONS

Niwa, et al., "Agr. Biol. Chem.", vol. 34, No. 6, pp. 966–968, 1970.

Koba, et al., "Agr. Biol. Chem.", vol. 40, No. 6, pp. 1167–1173, 1976.

Murao, et al., "Agric. Biol. Chem.", vol. 41, No. 6, pp. 919–924, 1977.

Primary Examiner—Johnnie R. Brown
Attorney, Agent, or Firm—Craig & Antonelli

[57] ABSTRACT

An amino sugar compound represented by the general formula:

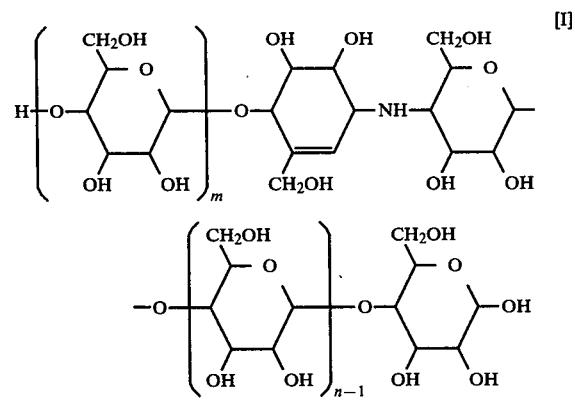

(wherein m is an integer of 0 to 8, n is an integer of 1 to 8 and m+n is an integer of 1 to 8) has strong glycosidase inhibiting action and is produced by culturing an amino sugar compound producing microorganisms belonging to Streptomyces.

9 Claims, 2 Drawing Figures

AMINO SUGAR COMPOUND

The present invention relates to a novel amino sugar produced by an amino sugar compound producing microorganism belonging to the genus Streptomyces and a method for producing same.

The present inventors have found that Actinomyces A2396 strain separated from soil of paddy field in Shimomata, Kakegawa-shi, Siquoka-ken, Japan produces a novel amino sugar which is a useful amylase inhibiting substance.

The present invention based on the above discovery relates to a novel amino sugar compound [I] explained hereinafter and a method for producing the amino sugar compound [I] which comprises culturing an amino sugar compound [I] producing microoganism belonging to the genus Streptomyces in a culture medium and recovering the amino sugar compound [I] therefrom.

It is an object of the present invention to provide the amino sugar compound [I] having a strong and specific inhibiting action against, glycosidases such as amylase, succharase, maltase, etc. and a method for producing same. This amino sugar compound [I] has the action of inhibiting the carbohydrate metabolism in human beings and animals and so is useful for treatment of, for example, diabetes, obesity, and pseudohypertrophia lipomatosa, secondary diseases caused by said abnormal metabolism, and moreover diseases caused by sugar metabolism by microorganism in the mouth such as decayed tooth, etc.

Figure 2:
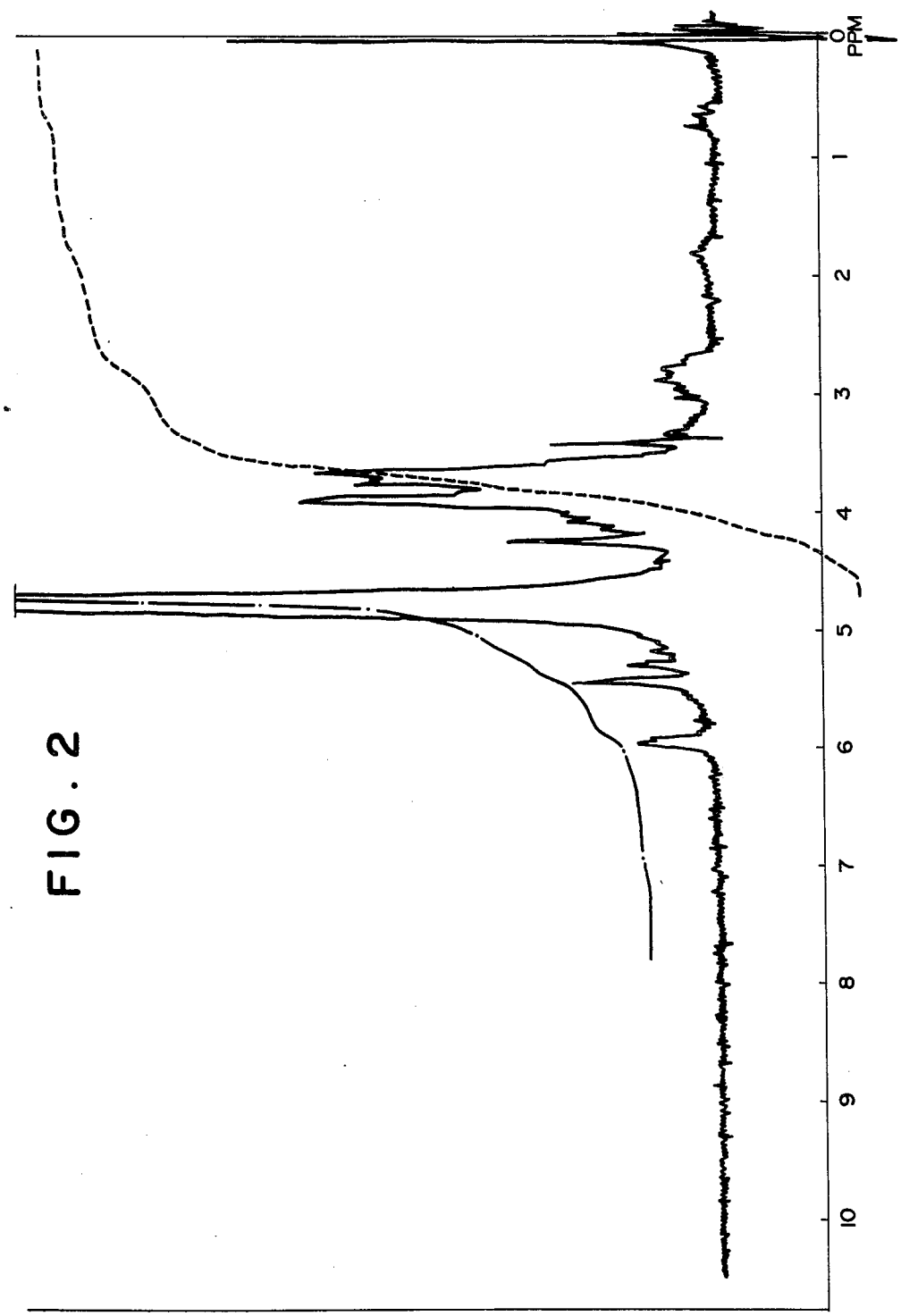

In the accompanying drawings,

FIG. 1 and FIG. 2 show infrared absorption spectrum and nuclear magnetic resonance spectrum of the present compound, respectively.

It has been found that said amino sugar compound [I] is a novel amino sugar compound (referred to as amino sugar compound [I] hereinafter) represented by the general formula [I]:

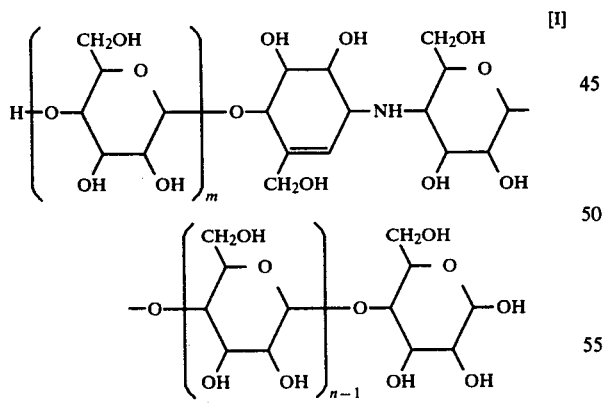

[wherein m is an integer of 0 to 8, n is an integer of 1 to 8 and m+n is an integer of 1 to 8].

Physicochemical properties of the novel amino sugar compound [I]

The amino sugar compound [I] of the present invention has the following physicochemical properties.
 (1) Amino sugar compound represented by the general formula [I] (wherein n=1 and m=0).
   (1) Molecular formula $C_{19}H_{33}O_{14}N$
   (2) Molecular weight 499 (according to mass spectrum method)
   (3) Ultraviolet absorption spectrum (solvent: water and concentration: 10 γ/ml) ... end type absorption
   (4) Infrared absorption spectrum (by KBr method): Spectral lines are as shown in FIG. 1.
   (5) Solubility in solvents: soluble in water, methanol, dimethylformamide, dimethylsulfoxide, and hot ethanol and insoluble in acetone, ethyl acetate and chloroform
   (6) Color reaction: positive in anthrone, potassium permanganate, and sulfuric acid and negative in ninhydrin reaction and ferric chloride reaction.
   (7) Weakly basic white powders.
   (8) Thin-layer chromatography using ethyl acetate, methanol and water in a ratio of 10:6:4 as solvent and silica gel F254 (produced by Merck & CO., Inc.). Detection is carried out with silver nitrate-sodium hydroxide to obtain Rf 0.32.
   (9) Mass spectrum
     Acetyl form (pyridine-acetic anhydride method) Main peaks are 961 (undecaacetyl form), 902, 901, 842, 841, 817
     Methyl form (dimethylsufoxide-$CH_3I$/NaH method) 667 (dodecamethyl form), 663 (undecamethyl form) 565
   (10) Nuclear magnetic resonance spectrum: The nuclear magnetic resonance spectrum of the compound of the present invention with 100 MHz, inner standard substance DSS and solvent $D_2O$ is as shown in FIG. 2.
   (11) Methylation → hydrolysis → $NaBH_4$ reduction → acetylation and then gas chromatography analysis result in 1,4,5-tri-o-acetyl-2,3,6-tri-o-methyl-D-glucitol.
   (12) Optical rotation: $[\alpha]_D + 153°$ (solvent: water and concentration: 1%)
   (13) Elementary analysis: C:42.86, H:6.44, N:2.42
   (14) Sugar content according to anthrone method: 60%
   (15) Amylase inhibitor unit (AIU/mg): $3.4 \times 10^2$ The above data of spectrum and chemical properties provide the following structural formula for this compound.

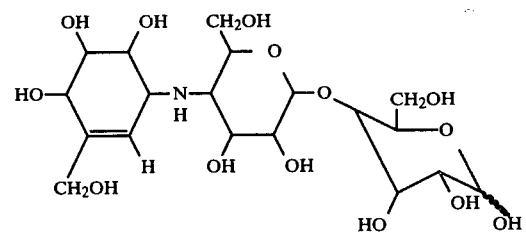

(2) Amino sugar compound represented by the formula [I] (wherein n=2 and m=0).
   (1) Molecular formula $C_{25}H_{43}O_{19}N$
   (2) Molecular weight 661 (according to mass spectrum method)
   (3) Ultraviolet absorption spectrum: End type absorption
   (4) Solubility in solvents: soluble in water, methanol, dimethylformamide, dimethylsulfoxide, and hot ethanol and insoluble in acetone, ethyl acetate and chloroform.

(5) Color reaction: positive in anthrone, potassium permanganate and sulfuric acid and negative in ninhydrin reaction and ferric chloride reaction.
(6) Weakly basic white powder.
(7) Thin-layer chromatography using ethyl acetate, methanol and water in a ratio of 10:6:4 as solvent and silica gel F254 (produced by Merck & Co., Inc.). Detection is carried out with silver nitrate-sodium hydroxide to obtain Rf of 0.25.
(8) Mass spectrum: Methyl form (dimethylsulfoxide-$CH_3I$/NaH method) Main peaks are 871 (15 methyl form), 857 (14 methyl form), 769, 622, 565, 418, 416, 315, 217, 201, 131, 118 and 105. Acetyl form (pyridine-acetic anhydride method) 1249 (14-acetyl form), 1190, 1189, 1131, 1130, 1105, 902, 842, 782, 739, 614, 554 and 494.

(1) Hydrolysis with an acid provides a compound represented by the general formula [I] (wherein n=1, m=0) and glucose.
(2) Thin-layer chromatography using ethyl acetate, methanol and water in a ratio of 10:6:4 as solvent and silica gel F254 (produced by Merck & Co., Inc.) Rf 0.18
(3) Sugar content by anthrone method: 74%
(4) Methylation → hydrolysis → $NaBH_4$ reduction → acetylation and then gas chromatography provide only 1,4,5-tri-o-acetyl-2,3,6-tri-o-methyl-D-glucitol
(5) Amylase inhibitor unit (AIU/mg) $1.4 \times 10^3$ The above data of spectrum and chemical properties provide the following structural formula for the compound.

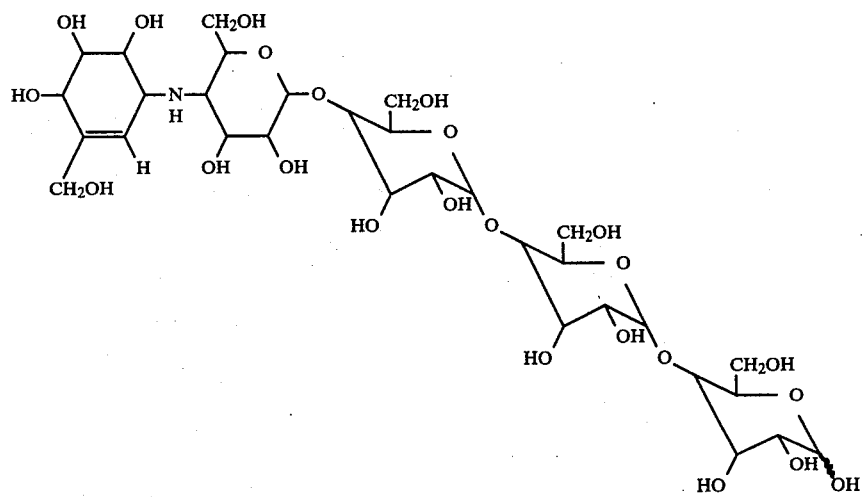

(9) Elementary analysis: C:42.78, H:6.65, N:1.81
(10) Optical rotation $[\alpha]_D + 127°$ (water and concentration 1%)
(11) Sugar content by anthrone method: 67%
(12) Methylation → hydrolysis → $NaBH_4$ reduction → acetylation and then gas chromatography result in only 1,4,5-tri-o-acetyl-2,3,6-tri-o-methyl-D-glucitol.
(13) Thin chromatrography analysis of compound obtained by partial hydrolysis with acid provides a compound represented by the general formula [I] (wherein n=1, m=0) and glucose.
(14) Amylase inhibitor unit (AIU/mg) $3.6 \times 10^2$ The above data of spectrum and chemical properties provide the following structural formula for the compound.

(4) Amino sugar compound represented by the general formula [I] (wherein n=2, m=1)
(1) Hydrolysis with an acid provides a compound represented by the general formula [I] (wherein n=1, m=0) and glucose
(2) Thin-layer chromatography: Ethyl acetate, methanol and water as solvent in a ratio of 10:6:4 and silica gel F254 (produced by Merck & Co., Inc.) are used to obtain Rf of 0.18. Ethyl acetate, methanol, water and 25% ammonia in a ratio of 100:60:40:2 as solvent and silane-treated silica gel (produced by Merck & Co., Inc.) are used to find that mobility in the case of multiple times (3 to 5) is smaller than that of the compound represented by the general formula [I] (wherein n=1, m=0).
(3) Sugar content by anthrone method: 74%

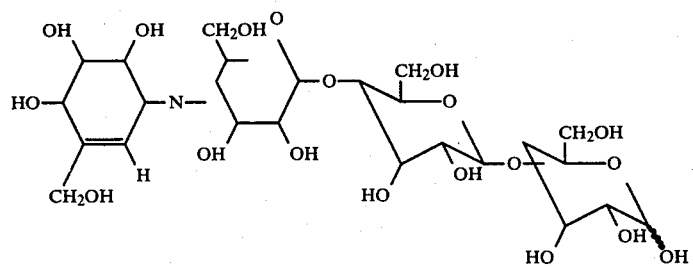

(3) Amino sugar compound represented by the general formula [I] (wherein n=3, m=0)

(4) Methylation → hydrolysis → $NaBH_4$ reduction → acetylation and then gas chromatography provide 1,4,5-tri-o-acetyl-2,3,6-tri-o-methyl-D-glucitol and 1,5-di-o-acetyl-2,3,4,6-tetra-o-methyl-D-glucitol in a ratio of 2:1.

(5) Amylase inhibitor unit (AIU/mg) $1.2 \times 10^3$

The above data of spectrum and chemical properties provide the following structural formula for the compound.

(3) Amylase inhibitor unit (AIU/mg) $1.9 \times 10^4$ (6) Amino sugar compound represented by the general formula [I] (wherein n+m=5 to 7)
  (1) Sugar content according to anthrone method: 87%
  (2) Thin-layer chromatography: Ethyl acetate, methanol and water in a ratio of 10:6:4 as solvent

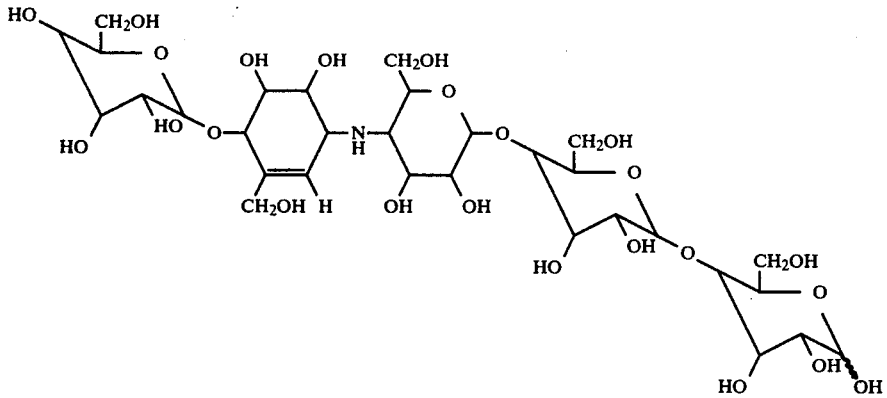

(5) Amino sugar compound represented by the general formula [I] (wherein n+m=4 to 6)
  (1) Sugar content according to anthrone method: 83%
  (2) Thin-layer chromatography: Ethyl acetate, methanol and water in a ratio of 10:6:4 as solvent and silica gel F254 (produced by Merck & Co., Inc.) are used to obtain Rf of 0.13 to 0.07.

and silica gel F254 (produced by Merck & Co., Inc.) are used to obtain Rf of 0.09 to 0.04.

(3) Amylase inhibitor unit (AIU/mg) $3.5 \times 10^4$

Comparison with known analogous substances

The amino sugar compounds of the present invention and known analogous substances are compared as follows:

| No. | Microorganism | Characteristics | Literatures |
|---|---|---|---|
| 1. | Actinoplanes | $R_1$ = (glucose)$_n$<br>n + m = 1 to 7<br>$R_2$ = (glucose)$_m$ | Japanese Patent Pre-examined Publication (Kokai) No. 53593/75 and No. 122342/77 |
| 2. | Streptomyces | The three components A, B and C are all sugar peptides. Positive in ninhydrin reaction | Agr. Biol. Chem. 40 1167(1976) |
| 3. | Actinomycetes | Mainly composed of glucose. Molecular weight 600. Main action is glucoamylase action. Glucoamylase inhibiting action >> α-amylase action (about 1/20 time). Acidic substance. No optical activity. | Japanese Patent Pre-examined Publication (Kokai) No. 54990/76 and Japanese Patent Post-examined Publication (Kokoku) No. 24119/77 |
| 4. | Streptomyces | Amilostatin A Neutral substance | Agr. Biol. Chem. 41 (6) 919-924 1977 Japanese Patent Post-examined Publication (Kokoku) No. 21596/77 and No. 21597/77 |
| 5. | Streptomyces | Nozirimycin | Agr. Biol. Chem. |

| No. | Microorganism | Characteristics | Literatures |
|---|---|---|---|
| 6. | Bacillus | [structure: cyclitol with CH₂OH, NH, OH groups] BPI Pluranase-inhibiting activity | 34 966 (1970) Abridgement of Lecture in Meeting of Japan Agricultural Chemistry, 51 184 (1976) |
| 7. | Streptomyces | [structure with R₁, R₂, NH, CH₂OH, OH groups] $R_1 = (glucose)_n$ $R_2 = OH$ or $(glucose)_m$ $n + m = 1$ to $7$ | The substance of the present invention |

Note:
1 and 5 are clearly different in structure. Substance 7 which is the substance of the present invention is a basic substance negative in ninhydrin reaction and so is different from 4 and 2. Substance 7 is different from substance 3 in that the former is all weakly basic and has optical activity while the latter is an acidic substance and has no optical activity. The substance 7 is also different from substance 6 because the former is strong in $\alpha$-amylase action. Moreover, the substance 7 is recognized to have succharase and maltase inhibiting actions and especially that of $n = 1$ to $3$ is strong in these actions.

From the above comparisons, it is recognized that the substance of the present invention is novel.

Oral administration of 1 g. of the substance of the present invention shows no toxicity.

The substance of the present invention can be orally administered in the form of tablet or syrup or administered by injection. Besides it can be used in admixture with beverages or foods.

Test method on amylase activity

The amylase activity of the novel amino sugar compound of the present invention was measured by the following method.

Amylase test in vitro

Amylase inhibitor unit (1 AIU) is defined as the amount of inhibitor required to control the amylase unit by about 50%. The amylase unit (AU) is the value of enzyme to divide 1μ equivalent of glucoside bond in starch for 1 minute under the following test conditions. The μ equivalent of this divided bond is determined as reduced μ equivalent of sugar formed by Kurie's method which uses dinitrosalicylic acid. Standard curve using maltose is given as μ equivalent of maltose equivalent. A testing solution (0–20 μl) in 0.4 ml of a solution (pH 6.9) containing 0.001 mol of $CaCl_2$, 0–10 μg of the inhibitor and 0.02 mol of sodium glycerophosphate is added to 0.1 ml of an amylase solution (20 to 22 AU/ml). This mixture is equilibrated in a water bath of 35° C. for about 10–20 minutes. Then, this is cultured at 35° C. for 5 minutes together with 0.5 ml of a 1% starch solution (soluble starch No. 1,252 from Marck, Darmstadt) preheated to 35° C. and thereafter 1 ml of dinitrosalicylic acid reagent (P. Bernfeld, Colowick-Kaplan, Meth. Enzymol., 1, 149) is added thereto. For developing color, the batch is heated in a boiling water bath for 5 minutes and then cooled and 10 ml of distilled water is added thereto. Absorbance of 540 nm is measured in comparison with blanks prepared in the same manner without using amylase. For evaluation, amylase activity which is still effective after addition of inhibitor is read from previously recorded amylase standard curve and inhibiting rate (%) of the amylase used is calculated from from said amylase activity. The inhibiting rate is plotted as function of the quotient:

$$\frac{\mu g \text{ inhibitor}^+}{AU^{++}}$$

$^+$dry substance
$^{++}$AU in the batch in the same series which has not been inhibited.

Inhibiting point of 50% is read from this curve and is converted to AIU/mg of the inhibitor.

Microbiological properties of Actinomycete producing amylase inhibiting substance The microbiological properties of Actinomycete strain A2396 used in the present invention are as follows:

I. Morphological characteristics

According to observation with naked eyes, aerial mycelium which formed mature spores has grayish brown color and substrate mycelium have yellow or yellowish orange color. Soluble pigment is not produced.

The strain is cultured on starch agar medium at 30° C. for 10 days and is observed under a light microscope to obtain the following results. Nearly the same form is observed on glucose asparagine, glycerin.asparagine, oat meal and yeast.malt agar media.

The aerial mycelium has a diameter of 0.6-0.8μ, is straight or wavy, extends forming simple branches and produces many chain spores. The chain of the spore is mostly hook-like or loop-like and rarely forms spiral of 2–3 turns. In the later stage of culture it becomes wetted the chain of the spore is broken (hygroscopic state).

The spore is egg-shaped, has a size of 0.8-1.0×1.0-1.5μ and has smooth surface image under electron microscope.

Substrate mycelium branch and extend in flexuous or wavy state and has a diameter of 0.5-0.6μ. There is no division of substrate mycelium nor formation of spores. Flagellum spores and sporangium are not produced.

II. Composition of diaminopimelic acid

L-diaminopimelic acid was detected.

III. Cultural characteristics

The cultural characteristics observed after cultivation at 30° C. for 20 days on the various media are shown below. (Color harmony manual, the 4th edition* is referred to for color.)
*Container Corporation of America, U.S.A., Color harmony manual 4th ed. 1958.

(1) Sucrose-nitrate agar medium
   Growth: nearly no growth
(2) Glycerin-nitrate agar medium
   Growth: moderate; Colonial Yellow-(2 ga) to Light wheat (2 ea)
   Aerial mycelium: moderate; White (a), spots of light tan (3 gc)
   Soluble pigment: none
(3) Glucose-asparagine agar medium
   Growth: moderate or poor; colorless to Light Ivory (2 ca)
   Aerial mycelium: trace or poor; Camel (31 e), spots of Beaver (31 i)
   Soluble pigment: none
(4) Glycerin-asparagine agar medium
   Growth: moderate; Light Wheat (2 ea) to Honey Gold (2 ic)
   Aerial mycelium: moderate; Adobe Brown (31 g) to Beaver (31 i)
   Soluble pigment: none
(5) Starch agar medium
   Growth: moderate; Mustard Gold (2 pe) to Amber (3 pc)
   Aerial mycelium: Bisque (3 ec) to Beige (3 ge), spots of Beaver
   Soluble pigment: none
(6) Tyrosine agar medium
   Growth: moderate or good; Bamboo (2 gc) to Honey Gold (2 ic)
   Aerial mycelium: moderate or good; Adobe Brown (31 g) to Beaver (31 i)
   Soluble pigment: none
(7) Oat.meal agar medium
   Growth: moderate; Light Ivory (2 ca) to Light Wheat (2 ea)
   Aerial mycelium: moderate; Bisque (3 ec) to Beaver (31 i)
   Soluble pigment: none
(8) Yeast.malt agar medium
   Growth: good; Mustard Gold (2 pe) to Amber (3 pe)
   Aerial mycelium: moderate; Camel (3 ie), spots of Beaver (31 i)
   Soluble pigment: none
(9) Bennett's agar medium
   Growth: moderate; Mustard Gold (2 pe)
   Aerial mycelium: poor; Beige (3 ge)
   Soluble pigment: none
(10) Nutrient agar medium
   Growth: poor; Light Wheat (2 ea)
   Aerial mycelium: none
   Soluble pigment: none
(11) Peptone.yeast iron agar medium
   Growth: moderate; Light Ivory (2 ca) to Light Wheat (2 ea)
   Aerial mycelium: none
   Soluble pigment: none IV. Physiological characteristics (1) Growth temperature range: 13°-46° C.
(2) Liquefaction of gelatin: positive
(3) Hydrolysis of starch: positive
(4) Coagulation and peptonization of skin milk: positive in both.
(5) Formation of melanoid: negative
(6) Assimilability of carbon source
   Positive: L-arabinose, D-xylose, D-glucose, D-fructose and inositol
   Negative: Sucrose, L-rhamnose, L-raffinose and D-mannitol As mentioned above, A2396 strain produces aerial mycelium having many spore chains from true substrate mycelium which does not cause fission and it contains L-diaminopimelic acid. From these facts, it was considered to belong to Streptomyces and named Streptomyces sp. A2396.

This strain has been deposited at Fermentation Research Institute, Agency of Industrial Science and Technology, Japan, bearing Acceptance No. 4275.

Culture and recovery

The said Streptomyces sp. A2396 strain is merely one example of the strains used in the present invention and all of amino sugar compound [I] producing strains can be used in the present invention.

The present invention will be illustrated below with reference to the use of Streptomyces sp. A2396 strain.

The ordinary culture process for producing amino sugar compound [I] using said strain was effected. Culture process may be either liquid or solid culture. Industrially, it is preferred to inoculate a suspension of spores of said amino sugar compound [I]-producing microorganism or a culture solution cultured for 2-3 days and to effect deep aeration shaking culture.

As nutrients for medium, those which are generally used for culture of microorganism are widely used. As carbon sources, assimilable carbon compounds may be used. Examples thereof are glucose, sucrose, lactose, maltose, starch, molasses, glycerin, etc. As nitrogen source, assimilable nitrogen compounds may be used. Examples thereof are corn steep liquor, soybean meal, wheat gluten, peptone, meat extract, yeast extract, casein hydrolyzate, various ammonium salts, nitrates, etc.

Furthermore, phosphates, sulfates and salts of magnesium, calcium, potassium, sodium, iron, zinc, manganese, etc. may also be used, if desired.

Culturing temperature can be suitably selected from the range where the strain grows to produce the amino sugar compound [I]. Preferable range is from 26° to 33° C. Culturing time varies depending on the conditions, but usually is about 3 to 4 days at 26° to 32° C. After potency of the amino sugar compound [I] seems to reach max, culture may be effected for suitable period of time.

Amino sugar compound [I] is mostly produced in liquid portion in the liquid cultured broths of strain producing the amino sugar compound [I].

The amino sugar compound [I] is recovered from the cultured broths by treating the culture filtrate with active carbon under acidic state to adsorb impurities (the amino sugar compound [I] is not adsorbed because this is acidic), then filtering off the active carbon, neutralizing the filtrate, thereafter again treating the filtrate with active carbon to adsorb the amino sugar compound [I], then subjecting the active carbon to elution with 50-60% acetone water, treating the solution of crude substance with ion exchange resin at strongly acidic state and recovering active fraction.

EXAMPLE 1

Recovery of crude product from cultured broths

A2396 strain was inoculated from slant to a 500 ml conical flask containing 100 ml of a sterilized nutrient solution which had a composition of soluble starch 1%, glucose 1%, soybean meal 1.5%, $K_2HPO_4$ 0.1%, NaCl 0.3% and $MgSO_4$ 0.1% and which was adjusted to a pH of 7.2 with NaOH before sterilization and this mixture was cultured on a rotary shaker at 30° C. for 48 days. This culture solution was inoculated to a jar-fermentor (30 l) containing 20 l of medium having said composition and cultured at 30° C. for 72 hours. A suitable amount of perlite was added to 60 l of thus obtained cultured broth and this was subjected to filtration. The pH of the filtrate was adjusted to 2.0 with half concentrated nitric acid and 600 g of active carbon and 2,400 g of perlite were added. The mixture was stirred for 15 minutes and then filtered. The filtrate was neutralized with ammonium hydroxide solution and thereafter was stirred for 30 minutes together with 1,200 g of active carbon.

This mixture was filtered by filter press and precipitate of active carbon was washed 3 times with 10 l of distilled water. Then, the active carbon was pressed and well dried and was stirred for 15 minutes in 4 l of 50% aqueous acetone solution of pH 2.5 to elute active substance from the active carbon. This operation was repeated three times. Then, the active carbon was removed by filtration and then the eluates were combined. The eluate was concentrated to 250 ml in a rotary evaporator under reduced pressure and the equal volume (250 ml) of methanol was added thereto. The mixture was filtered with a filter. The filtrate (480 ml) was dropped in 5 l of acetone with vigorous agitation, the resultant precipitate was filtered and the precipitate was washed with acetone and ether three times and then vacuum dried to obtain 100 g of white powder.

The resultant white powder was dissolved in 330 ml of distilled water. The solution was added to a column of 8 cm×20 cm packed with ion exchange resin IR-120 ($H^+$) (Trade Mark; manufactured by Rohm & Haas Co.) at a flow rate of 50 ml/min., furthermore was washed with distilled water and thereafter eluted with a 2% ammonium hydroxide solution. The eluate was divided at 20 ml/fractions and fractions No. 30 and No. 50 were taken. Said amylase inhibiting active fractions were collected and concentrated under reduced pressure to dryness to obtain 5.0 g of brown powder. Then, this powder was dissolved in 100 ml of distilled water. This solution was added to a column of 3.5 cm×90 cm packed with ion exchange resin Dowex 50×8 (Trade Mark; manufactured by Dow Chemical Co.) (particle size 200-400 meshes) at a flow rate of 10 ml/min, washed with water and furthermore successively eluted with 900 ml of 0.1 M pyridine-formic acid solution at pH 3.1, 900 ml of 0.2 M pyridine-formic acid solution at pH 3.1 and 900 ml of 0.2 M pyridine-formic acid solution at pH 4.4 in this order. The eluate was divided at 20 ml/fraction. Fractions No. 20 to No. 35 were called A, fractions No. 64 to No. 82 were called B and fractions No. 110 to No. 128 were called C and each fraction was concentrated to dryness. Fraction A which is shown in Example 5 contained amino sugar compounds of $m+n=3$, $m+n=4$ to 6 and $m+n=5$ to 7 in the general formula [I] [referred to as $(m+n=3)$ compound, $(m+n=4$ to 6$)$ compound and $(m+n=5$ to 7$)$ compound hereinafter], respectively, and fraction B which is shown in Example 4 contained amino sugar compound of $n=2$, $m=0$ in the general formula [I] [referred to as (2-0) compound hereinafter]. Said fraction C which is shown in Example 3 contained amino sugar compound of $n=1$, $m=0$ in the general formula [I] [referred to as (1-0) compound hereinafter].

EXAMPLE 2

A2396 strain was inoculated from slant to a 500 ml conical flask containing 100 ml of a sterilized nutrient solution which had a composition of soluble starch 2%, glucose 1%, soybean meal 1.5%, $K_2HPO_4$ 0.1%, NaCl 0.3% and $MgSO_4$ 0.1% and which was adjusted to a pH of 7.2 with NaOH before the sterilization and this mixture was shaking cultured at 30° C. for 48 days on a rotary shaker. 2 l of this cultured broth was transferred to a 250 l tank containing 200 ml of a sterilized medium having the composition of soluble starch 2%, soybean meal 1.5%, $K_2HPO_4$ 0.1%, NaCl 0.3%, and $MgSO_4$ 0.1% and culture was carried out at 30° C. for 72 hours. To this cultured broth was added 2 Kg of zeolite and filtration was effected to obtain 180 l of a filtrate. To this filtrate was added 4 Kg of active carbon and active substance was adsorbed thereto. Thereafter, the active carbon was filtered off and furthermore washed with water. The active carbon washed with water was extracted with 20 l of 50% aqueous solution of acetone three times. Thus obtained aqueous acetone solution was concentrated to 1 l under reduced pressure and 10 l of acetone was added thereto to cause precipitation. The precipitate was filtered off and then powdered (yield . . . 300 g).

300 g of the resultant powder was dissolved in 1 l of water. The solution was added to a column of 8 cm×20 cm packed with ion exchange resin [Dowex 50 W ($H^+$), Trade Mark; particle size 200-400 meshes] to be adsorbed to the resin. The adsorbed active substance was eluted with 1 N aqueous $NH_4OH$ solution. The eluate was divided at 20 ml/fraction to obtain fractions No. 15 to No. 35 (400 ml) which had amylase inhibiting action. Thus obtained active fractions were concentrated and then precipitation was allowed to occur with acetone to obtain 30 g of light yellow powder.

3 g of the thus obtained powder was dissolved in water and the solution was filled in a column of 3 cm×30 cm packed with ion exchange resin [CM-Sephadex ($H^+$), Trade Mark; (manufactured by Pharmacia Fine Chemicals Inc.) which was dextran gel having carboxymethyl group as exchange group which was adjusted to a pH of 3.0 with hydrochloric acid], washed with distilled water and thereafter eluted with a gradient prepared from 500 ml of distilled water and 500 ml of 0.3 M NaCl. The eluate was divided at 20 ml/fraction. Fractions (Nos. 13 to 18) active in amylase inhibiting action were collected and concentrated. This was adsorbed to a small amount of active carbon and subjected to desalting. Thereafter, this was again concentrated and furthermore acetone was added to obtain a precipitate as powder. This product was nearly pure as the active substance of the present invention, but it was a mixture of homologous compounds mainly composed of amino sugar compounds represented by the general formula [I] (wherein n=3 to 7).

EXAMPLE 3

The powder dispensed from the fraction C in Example 1 and containing the amino sugar compound [(1-0) compound] of the present invention was dissolved in a small amount of water-containing ethanol. This solution was added to a silica gel column (2 cm×20 cm) previously wetted with a mixture of butanol:ethanol:water(5:1:1), adsorbed thereto and then developed with a mixed liquid of butanol:ethanol:water(5:1:1). The eluate was divided at 10 ml/fraction. Each fraction was subjected to the test on amylase inhibition action, the test on sugar content by anthrone method and the thin-layer chromatography test and the fractions (No. 15 to No. 25) which contained said (1-0) compound were collected. They were concentrated under reduced pressure and thereafter ethanol was added to cause precipitation to occur and 60 mg of said pure (1-10) compound was obtained as dry powder.

EXAMPLE 4

The powder dispensed from the fraction B in Example 1 and containing the amino sugar compound [(2-0) compound] was dissolved in a slight amount of water-containing ethanol. This solution was added to a silica gel column (2 cm×20 cm) previously wetted with a mixed liquid of butanol:ethanol:water(5:1:1), adsorbed thereto and then developed with a mixed liquid of butanol:ethanol:water(5:1:1). The eluate was divided at 10 ml/fraction. Each fraction was subjected to the test on amylase inhibiting action, the test on sugar content by anthrone method and thin-layer chromatography test with silica gel and the fractions (No. 24 to No. 32) containing said (2-0) compound were collected. They were concentrated under reduced pressure and ethanol was added to cause precipitation to occur to obtain 75 g of pure (2-0) compound as dry powder.

EXAMPLE 5

The fraction A in Example 1 was concentrated to dryness under reduced pressure and dissolved in a slight amount of water. The solution was added to silica gel column (2 cm×20 cm) previously wetted with a mixed liquid of butanol:ethanol:water(5:1:1) to adsorb thereto and then this was developed with a mixed liquid of butanol:ethanol:water(5:1:1). The eluate was divided at 10 ml/fraction and the fractions (No. 30 - No. 47) having amylase inhibiting action and activity were collected and concentrated to dryness. Then, this was dissolved in a small amount of distilled water and then was gel filtered with a column (1.5 cm×95 cm) packed with Sephadex G-10. Each of the obtained fractions (2 ml/fraction) was subjected to the test on amylase activity, the test on sugar content by anthrone method and thin-layer chromatography test to obtain the present amino sugar compound [(m+n=3) compound] from fractions No. 38 - No. 43, the present amino sugar compound [(m+n=4 to 6) compound] from fractions No. 30 to No. 35 and the present amino sugar compound [(m+n=5 to 7) compound] from fractions No. 23 to No. 30, respectively. Each fraction was concentrated and thereafter ethanol was added to cause precipitation to obtain 70 mg of pure (m+n=3) compound, 80 mg of (m+n=4 to 6) compound and 100 mg of (m+n=5 to 7) compound as dry powder, respectively.

EXAMPLE 6

10 g of active substance containing mainly the present amino sugar compound [(n+m=3 to 7) compound] dispensed from the fraction A in Example 2 was dissolved in an aqueous sulfuric acid solution of 4 ml of concentrated sulfuric acid and 50 ml of distilled water and the solution was hydrolyzed for 30 minutes under reflux (bath temperature 104° C.), by which the amino sugar compounds having greater (m+n) value in the general formula [I] were hydrolyzed. Thus obtained blackish brown solution was neutralized in a 10 N sodium hydroxide solution. The obtained solution was well stirred together with 1 g of active carbon to adsorb the active substance to the active carbon.

The active carbon to which the active substance was adsorbed was sufficiently washed with water and then was extracted with 10 ml of 50% aqueous acetone solution. The solution of the extracted active substance was concentrated and acetone was added to cause precipitation to obtain 3 g of powder.

3 g of this powder was dissolved in water and the solution was added to a column packed with 2.0 g of ion exchange resin [Amberlite IR 120 (H+)]. Then, the column was washed until glucose was not detected. Furthermore, this was eluted with 50 ml of 1% ammonium hydroxide solution. Thus obtained eluate was concentrated to dryness. Then, this was added to a silica gel column (4 cm×40 cm) previously wetted with a mixed liquid of butanol:ethanol:water(5:1:1) and was developed with a mixed liquid of butanol:ethanol:water(5:1:1).

The eluate was divided at 20 ml/fraction and each fraction was subjected to the test on amylase inhibiting action, the test on the sugar content by anthrone method and thin-layer chromatography test with silica gel by which the fractions No. 30 to No. 45 [(1-0) compound], and No. 55 to No. 64 [(2-0) compound] of active substance were collected. Each of them was concentrated and, furthermore desalted with ion exchange resin (Amberlite IR 120) to obtain 430 mg of pure (1-0) compound and 54 mg of (2-0) compound.

EXAMPLE 7

50 mg of the fraction of the present amino sugar compound [(m+n=3) compound] in Example 5 was dissolved in water. The solution was added to a silica gel column (2 cm×90 cm) packed with ion exchange resin [Dowex 50×4 (H+)] and adsorbed thereto. Thereafter, this was eluted with a 0.25 aqueous solution of HCl and the eluate was divided at 5 ml/fraction. Each fraction was subjected to the test on amylase inhibiting action and thin-layer chromatography test whereby the fractions Nos. 150-185 of active substance [(2-1) compound] and the fractions Nos. 190-196 [(3-0) compound] were collected. Each was concentrated and acetone was added thereto to obtain a powder. From said powder 20 mg of pure (2-1) compound and 3 mg. of pure (3-0) compound, respectively.

What is claimed is:

1. An amino sugar compound represented by the formula:

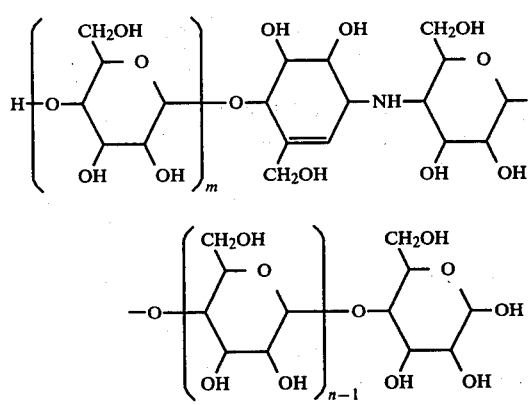

(wherein m is an integer of 0 to 8, n is an integer of 1 to 8 and m+n is an integer of 1 to 8).

2. An amino sugar compound according to claim 1, wherein m=0 and n=1 in the formula [I].
3. An amino sugar compound according to claim 1, wherein m=0 and n=2 in the formula [I].
4. An amino sugar compound according to claim 1, wherein m=0 and n=3 in the formula [I].
5. An amino sugar compound according to claim 1, wherein m=1 and n=2 in the formula [I].
6. An amino sugar compound according to claim 1, wherein m+n=4 in the formula [I].
7. An amino sugar compound according to claim 1, wherein m+n=5 in the formula [I].
8. An amino sugar compound according to claim 1, wherein m+n=6 in the formula [I].
9. An amino sugar compound according to claim 1, wherein m+n=7 in the formula [I].

* * * * *